United States Patent [19]
Clarke et al.

[11] Patent Number: 5,037,959
[45] Date of Patent: Aug. 6, 1991

[54] SELF INCOMPATIBILITY PROTEIN

[75] Inventors: Adrienne E. Clarke, Parkville, Australia; Elizabeth G. Williams, Lexington, Ky.; Marilyn A. Anderson, Sunbury, Australia; Shaio-Lim Mau, Wheelers Hill, Australia; Rosslyn Hoggart, Sassafras, Australia; Edwina Cornish, South Melbourne, Australia

[73] Assignee: Lubrizol Genetics, Inc., Wickliffe, Ohio

[21] Appl. No.: 50,747

[22] Filed: May 15, 1987

Related U.S. Application Data

[63] Continuation-in-part of Ser. No. 615,079, May 29, 1984, abandoned, and a continuation-in-part of Ser. No. 854,139, Apr. 21, 1986, abandoned, which is a continuation-in-part of Ser. No. 792,435, Oct. 29, 1985, abandoned.

[51] Int. Cl.$^5$ .................... C07K 15/10; C07K 15/14
[52] U.S. Cl. .................................... 530/370; 530/379; 530/395
[58] Field of Search .................. 530/370, 379, 395

[56] References Cited

PUBLICATIONS

Mau et al., 1982, Planta 156:505–516.
Bredemeijer et al., 1981, Theor. Appl. Genet. 59(3):185–190.
Bredemeijer et al., 1980, Theor. Appl. Genet. 57:119–123.
Nishio et al., 1979, Japan, J. Genetics 54:307–311.
Dickinson et al., 1982, Proc. R. Soc. Lond. B, 215:45–62.
Heslop-Harrison et al., 1982, Ann. Bot. 49:729–735.
Ebert et al., 1989, Genetic Polymorphism of Self-Incompatibility in Flowering Plants, Cell 56:255–262.

*Primary Examiner*—Margaret Moskowitz
*Assistant Examiner*—Keith C. Furman
*Attorney, Agent, or Firm*—Greenlee and Associates

[57] ABSTRACT

A class of proteins associated with self-incompatibility alleles of plants, preferably of gametophytic self-incompatibility type, are provided. These proteins inhibit pollen tube growth in a plant style having the associated self-incompatibility allele, and have defined amino acid homologies and cross-reactivities.

5 Claims, 13 Drawing Sheets

| | pI | Mr | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| L. peruvianum | | | | | | | | | | | | | | | | | |
| $S_1$ | 7.5 | 28000 | Y | F | E | Y | L | Q | L | V | L | Q | X | P | T | T | F |
| $S_3$ | >9.5 | 28000 | D | F | D | Y | L | Q | L | V | L | Q | X | P | R | S | F |
| N. alata | | | | | | | | | | | | | | | | | |
| $S_2$ | >9.5 | 32000 | A | F | E | Y | M | Q | L | V | L | T | W | P | I | T | F |
| $S_6$ | >9.5 | 31000 | A | F | E | Y | M | Q | L | V | L | Q | W | P | T | A | F |
| $S_7$ | 9.0 | 30000 | D | F | D | Y | M | Q | L | V | L | T | X | P | A | S | F |
| $S_{f11}$ | 9.5 | 27000 | D | F | E | Y | L | Q | L | V | L | T | W | P | A | S | F |

(Amino-terminal Sequence columns 1–15)

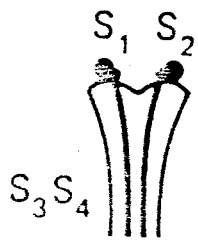
FIG. 1
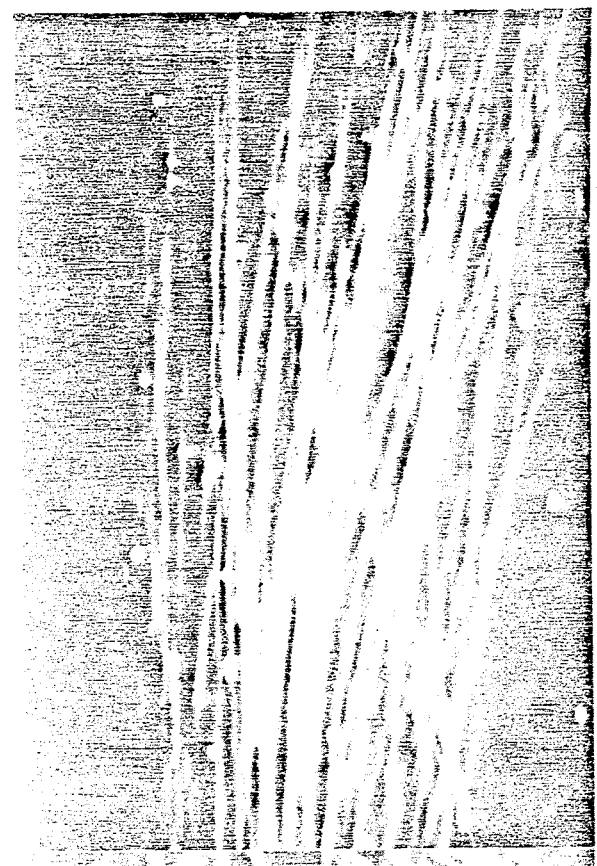
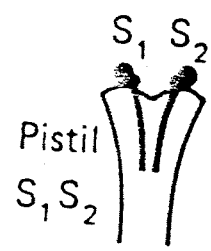
FIG. 2

FIG. 3

BEST AVAILABLE COPY $S_1S_3$　　　　　　　　　　　　$S_1S_2$ $S_1$　　　　　　　　　　　　　$S_1$
$S_3$　　　　　　　　　　　　　$S_2$ $S_2S_3$　　　　　　　　　　　　$S_3S_3$ $S_3$　　　　　　　　　　　　　$S_3$
$S_2$ $S_3S_4$　　　　　　　　　　　　$S_2S_2$ $S_3$
$S_4$　　　　　　　　　　　　　$S_2$

FIG. 4

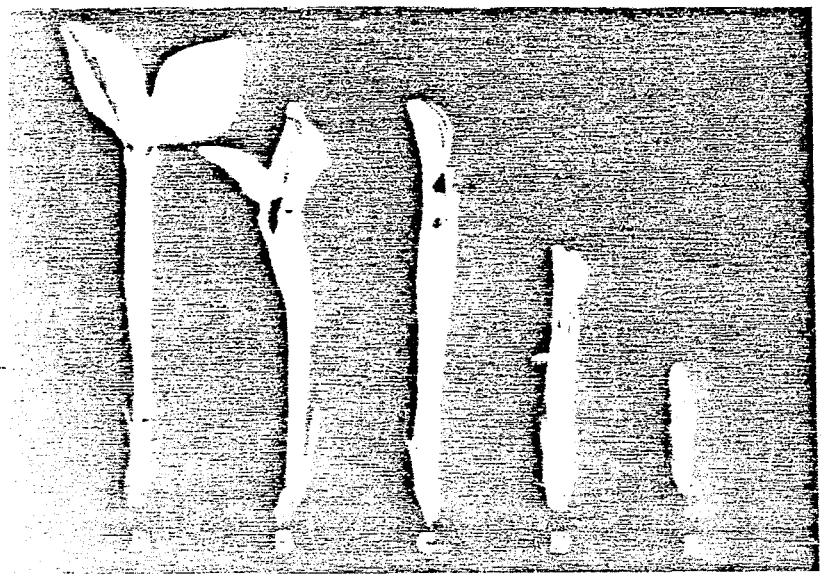
$S_2S_3$          $S_1S_3$
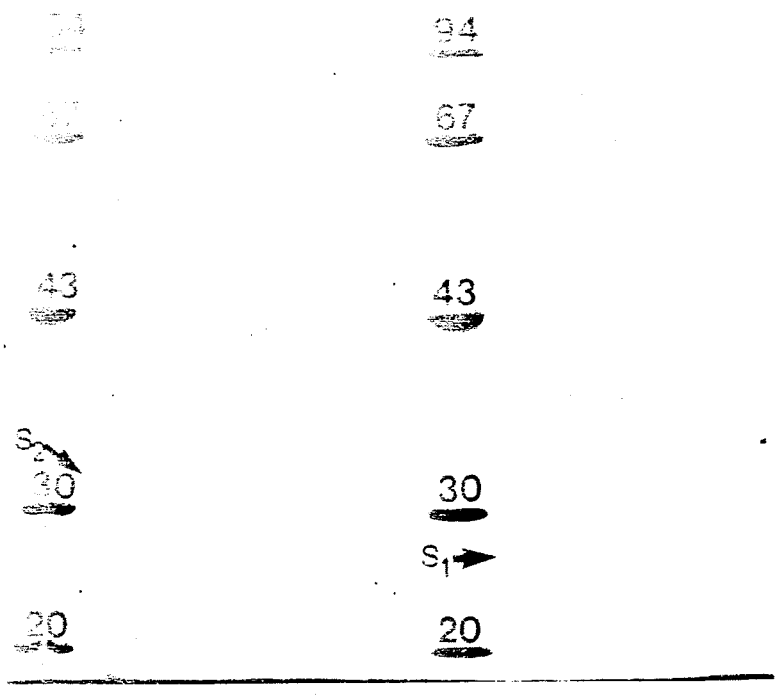
FIG. 6

BEST AVAILABLE COPY
Anti-<u>Brassica</u>-S
FIG. 13

FIG. 14

| | pI | Mr | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| L. peruvianum | | | | | | | | | | | | | | | | | |
| S1 | 7.5 | 28000 | Y | F | E | Y | L | Q | L | V | L | Q | X | P | T | T | F |
| S3 | >9.5 | 28000 | D | F | D | Y | L | Q | L | V | L | Q | X | P | R | S | F |
| N. alata | | | | | | | | | | | | | | | | | |
| S2 | >9.5 | 32000 | A | F | E | Y | M | Q | L | V | L | T | W | P | I | T | F |
| S6 | >9.5 | 31000 | A | F | E | Y | M | Q | L | V | L | Q | W | P | T | A | F |
| S2 | 9.0 | 30000 | D | F | D | Y | M | Q | L | V | L | T | X | P | A | S | F |
| Sf11 | 9.5 | 27000 | D | F | E | Y | L | Q | L | V | L | T | W | P | A | S | F |

Amino-terminal Sequence

FIG. 15

Ala Phe Glu Tyr Met Gln Leu Val Leu Thr

Trp Pro Ile Thr Phe Cys Arg Ile Lys His Cys Glu Arg Thr Pro Thr Asn Phe Thr Ile

His Gly Leu Trp Pro Asp Asn His Thr Met Leu Asn Tyr Cys Asp Arg Ser Lys Pro

Tyr Asn Met Phe Thr Asp Gly Lys Lys Asn Asp Leu Asp Glu Arg Trp Pro Asp Leu

Thr Lys Phe Asp Ser Leu Asp Lys Gln Ala Phe Trp Lys Asp Glu Tyr Val Lys

His Gly Thr Cys Cys Ser Asp Lys Phe Asp Arg Gln Tyr Phe Asp Leu Ala Met Thr

Leu Arg Asp Lys Phe Asp Leu Leu Ser Ser Leu Arg Asn His Gly Ile Ser Arg Gly Phe

Ser Tyr Thr Val Gln Asn Leu Asn Asn Thr Ile Lys Ala Ile Thr Gly Gly Phe Pro Asn

Leu Thr Cys Ser Arg Leu Arg Glu Leu Lys Glu Ile Gly Ile Cys Phe Asp Glu Thr Val

Lys Asn Val Ile Asp Cys Pro Asn Pro Lys Thr Cys Lys Pro Thr Asn Lys Gly Val Met

Phe Pro

5,037,959

SELF INCOMPATIBILITY PROTEIN

CROSS REFERENCE TO RELATED APPLICATIONS

This application is a continuation in part of application No. 615,079, filed May 29, 1984, now abandoned, and of co-pending application No. 854,139, filed Apr. 21, 1986, now abandoned, which is a continuation-in-part of application No. 792,435, filed Oct. 29, 1985, now abandoned, all of which are incorporated herein by reference.

BACKGROUND OF THE INVENTION

1. Field of the Invention

This invention relates to the identification and isolation in substantially pure form of an antigenic protein material from mature styles of self-incompatible plants, particularly members of the Solanaceae and the Cruciferae families, as exemplified by *Nicotiana alata*, an ornamental tobacco, *Lycopersicon peruvianum*, a wild tomato, and *Brassica oleracea*, Brussel sprout. Studies of this style-specific material indicate that it corresponds to the self-incompatibility genotype of such self-incompatible plants, and is the product of the S-gene which controls self-incompatibility.

Accordingly, this material has potential for use in control of pollentube growth, for example, as a natural gametocide to control, induce, or promote self-incompatibility and interspecific incompatibility. The S-gene and its product can also be used in genetic manipulation of plants to create self-incompatible cultivars. Plants engineered in this way will be valuable for the economic production of hybrid seed. In summary, the utility of this material will be in (i) production of selfed seed in out-breeding crops; (ii) creation of new interspecific hybrid crops; and (iii) generation of methods for economic production of hybrid seed in currently self-compatible crops.

2. Description of the Related Art

Many plant species, including *Nicotiana alata* and *Lycopersicon peruvianum*, are self-incompatible, that is, they cannot be fertilized by pollen from themselves or by that of a plant of the same S- (or self-incompatibility) genotype. The molecular basis of self-incompatibility is believed to arise from the presence of S-gene protein material in the mature styles of the plants; in particular, as exemplified by *N. alata* and *L. peruvianum*, this S-gene protein material has now been shown to be present in extracts of plant styles at the developmental stages of buds at first show of petal color, and at the subsequent stages of maturation of open but immature flowers, and flowers having mature glistening styles. On the other hand, the S-gene protein material is not present in the earlier developmental stages of green bud and elongated bud.

In plants exhibiting self-incompatibility, where the same S-gene is present in both the pollen and the pistil, pollen tube growth is arrested in the style of the plant and fertilization fails to occur. In both incompatible and compatible pollinations, the initial events are apparently identical. The pollen tubes germinate and grow extracellularly between the stigma papillae and then between the cells of the transmitting tissue of the style, which are joined by plasmodesmata into vertical files. At maturity, the extracellular material becomes progressively less viscous so that the pollen tubes grow through an amorphous fluid matrix between files of cells. At some point within the style, the growth of incompatible tubes is arrested. The precise zone of the style at which this happens varies with the ambient temperature. The behavior of the pollen tubes during growth indicates that the reaction may involve contact between the growing pollen tube and the extracellular components of the style, in particular contact of the growing tube with S-gene protein material as discussed above.

For general reviews of self-incompatibility, see de Nettancourt (1977), *Incompatibility in Angiosperms.* Springer-Verlag, Berlin; Heslop-Harrison (1978), Proc. Roy. Soc. London B, 202:73; Lewis (1979) N. Z. J. Bot. 17:637; Pandey (1979), N.Z. J. Bot. 17:645 and Mulcahy (1983) Science 220:1247. Selfincompatibility is defined as the inability of female hermaphrodite seed plants to produce zygotes after self-pollination. Two types of self-incompatibility, gametophytic and sporophytic, are recognized. Gametophytic incompatibility is most common and in many cases is controlled by a single nuclear gene locus (S-locus) with multiple alleles. Pollen expresses its haploid S-genotype and matings are incompatible if the S-allele expressed is the same as either of the S-alleles expressed in the diploid tissue of the pistil. During both incompatible and compatible matings, pollen tubes germinate and grow through the stigma into the transmitting tissue of the style. Tube growth from incompatible pollen grains is arrested in the upper third of the style.

In sporophytic incompatibility, pollen behavior is determined by the genotype of the pollen-producing plant. If either of the two S-alleles in the pollen parent is also present in the style, pollen tube growth in inhibited. Unlike gametophytic systems, inhibition usually occurs at the stigma surface and not in the style. In sporophytic incompatibility, S-protein may be concentrated at or near the stigma surface. The gametophytic polyallelic system is considered to be the ancestral form of self-incompatibility in flowering plants, with the sporophytic system being derived from it (de Nettancourt 1977). The products of the S-gene in the two systems are considered to be structurally related.

There are five species of gametophytically self-incompatible plants and two species of sporophytically incompatible plants in which differences in style or stigma proteins apparently related to S-genotype have been detected electrophoretically or immunologically. In *N. alata*, an association between specific bands and three S-allele groups was demonstrated by isoelectric focussing of stylar extracts (Bredemeijer and Blaas (1981) Theor. Appl. Genet. 59:185). Two major antigenic components have been identified in mature styles of *Prunus avium*, one of which (S-antigen) was specific to a particular S-allele group (Raff, et al. (1981) Planta 153:125; and Mau, et al. (1982) Planta 156:505). The antigenic component, a glycoprotein, was isolated by gel-filtration and ion-exchange chromatography. Two dimensional sodium dodecylsulfate polyacrylamide gel electrophoresis (SDS-PAGE) resolved two components (molecular weights 37,000 and 39,000, respectively) which could correspond to the $S_3$ and $S_4$ products in the diploid stylar material of cultivars of $S_3S_4$ genotype. The material was a potent inhibitor of the in vitro growth of pollen tubes from a $S_3S_4$ cultivar (Williams, et al. (1982) *Planta* 156:517). Stylar components which correspond to the S-allele group and are effective antigens in rabbits were detected in *Petunia hybrida* as reported by Linskens (1960), Z. Bot. 48:126. Four of the stylar proteins of *Lilium longiflorum* separated by electrofocussing reportedly showed distinct differences before and after heat treatment of the styles at 50° C. The S-gene product is thought to be heat labile because self-incompatibility can be broken by heat-treatment at 50° C; hence the bands lost during heat treatment may have corresponded to S-gene products (Dickinson, et al. (1982), Proc. Roy. Soc. London B. 215:45). A protein of molecular weight 24,000 isolated from stylar canal fluid of *Trifolium pratense* by Heslop-Harrison (1982) Ann. Bot. 49:729, may be involved in self-incompatibility.

A glycoprotein corresponding to genotype $S_7$ of *Brassica campestris* has been isolated from extracts of stigmas by gel-filtration followed by affinity chromatography on Con-A-Sepharose (Trademark, Pharmacia, Inc. Uppsala, Sweden) then isoelectric focussing, Nishio and Hinata (1979) Jap. J. Genet. 54:307. The protein had a pI of 5.7, molecular weight (by SDS-PAGE) of 57,000 and contained protein and carbohydrate in the ratio 1:1.2. The protein was not present in styles or ovaries. Nishio and Hinata (1982) Genetics 100:641, used similar techniques to isolate S-specific glycoproteins from stigma extracts of *Brassica oleracea* plants homozygous for S-alleles $S_{39}$, $S_{22}$ and $S_7$. The glycoproteins had high pI's (10.3, 11.1 and 10.6 respectively) and contained protein and carbohydrate in the ratios of 1:0.05 ($S_7$ and $S_{22}$) and 1:0.2 ($S_{39}$) The apparent molecular weight (by SDS-PAGE) of glycoproteins $S_7$ and $S_{39}$ was 57,000. Glycoprotein $S_{22}$ was apparently heterogeneous; two dimensional SDS-PAGE resolved two components of molecular weights 60,000 and 65,000. Antisera raised to each isolated S-specific glycoprotein not only precipitated its homologous glycoprotein but also the other two S-specific glycoproteins of *B. oleracea* and the $S_7$-specific glycoprotein of *B. campestris* (Hinata et al (1982) Genetics 100:649). A similar S-specific glycoprotein was isolated by Ferrari, et al. (1981) Plant Physiol. 67:270, from a stigma extract of *B. oleracea* using different techniques. Pretreatment of $S_2S_2$ pollen with the glycoprotein prevented the pollen germinating on normally compatible stigmas, indicating that the preparation was biologically active. Another partial purification was reported by Ferrari et al. (1981) using sucrose gradient sedimentation and double diffusion tests in gels in which the proteins were identified by Coomassie Blue staining.

Peroxidase isoenzymes extracted from styles of *N. alata* were reported to be S-gene specific by Pandey (1967), Nature 213:669. Subsequently, Bredemeijer and Blass (1980) Theor. Appl. Genet. 57:119, using the same species were unable to find any relationship between S-genotype and the peroxidase isozyme pattern and concluded that the peroxidases were coded by genes closely linked to the S-locus. It had been suggested that one of the isoenzymes in *N. alata* styles is involved in pollen tube growth (Bredemeijer and Blass (1975) Acta Bot. Naerl. 24:37), but it was subsequently found that this isoenzyme occurs in the cortex of the style, but is absent from the transmitting tissue, the site of pollen tube growth (Bredemeijer (1979) Acta Bot. Neerl. 28:197). Nasrallah, et al. (1970) Heredity 25:23, and Nishio and Hinata (1977) Heredity 38:391, were unable to detect any relationship between S-genotype and the pattern of peroxidase isoenzymes in stigma extract of *B. oleracea*. Therefore, the possible role, if any, of peroxidase isoenzymes in the incompatibility reaction is unclear.

S-L. Mau et al. (1986) in an article entitled "Style proteins of a wild tomato (*Lycopersicon peruvianum*) associated with expression of self-incompatibility", Planta 169:184–191, published less than a year prior to the filing date hereof, discuss some of the work on which this application is based.

SUMMARY OF THE INVENTION

This invention describes purified proteins associated with self-incompatibility alleles of plants, preferably gametophytically incompatible plants such as those of the family Solanacae, and the genuses *Nicotiana*, and *Lycopersicon*, exemplified by the species *Nicotiana alata* and *Lycopersicon peruvianum*. As used herein, the term protein includes glycoprotein, that is to say a protein having one or more carbohydrate groups covalently bound thereto.

As used herein, the term "substantially purified form" means that the purified material migrates as a single component on SDS-PAGE, when stained either with silver stain or with Coomassie Blue stain, and N-terminal sequencing shows less than 5% contamination with other proteins. A "purified protein" is one in "substantially purified form".

A protein "associated with a self-incompatibility allele" has the ability to inhibit pollen tube growth in a plant style having the associated self-incompatibility allele.

The proteins of this invention in glycosylated form have a molecular weight preferably between about 20 kd and about 35 kd.

As a result of this work, glycoprotein materials have been identified in the 26,000 to 32,000 MW region of stylar extracts of self-incompatibility genotypes of *N. alata* and *L. peruvianum*. These glycoprotein materials in the approximately 30,000 MW region have been identified as the S-gene proteins as described hereinafter. The purified proteins of this invention include proteins associated with the self-incompatibility alleles $S_1$, $S_2$ and $S_3$ of *N. alata* and $S_1$, $S_2$, $S_3$ and $S_4$ of *L. peruvianum*.

The term S-gene protein is used hereinafter to designate a protein coded by the S-gene. A protein coded by the S-gene must fulfill the following criteria: (1) segregation with S-allele; (2) localization in extracellular sites in the style. It should be in the mucilage of hollow styles or in the walls or intercellular matrix of the transmitting tract cells of styles with solid transmitting tissues. That is, the protein must be located at the site of contact with the pollen tubes; (3) occurence of the protein in the developing style must be coincident with expression of self-incompatibility. In many species, self-incompatibility is not expressed in immature styles. The S-gene protein would not be expected to occur in such styles at these early developmental stages.

In the discussions of antibodies and antisera which follow hereinafter, unless otherwise specifically designated, the terms antibody and antiserum include both polyclonal and monoclonal antibodies and antisera.

Closely related, but distinct, glycoprotein materials are identified in SDS-PAGE gels which correspond to individual genotypes studied. For each genotype, the genotype-specific glycoprotein only appears as the flower matures, and is detected only in style extracts of buds at first show of petal color and in later stages of maturation, but not in the earlier bud stages. Two-dimensional gels confirm the genotype-specificity of these glycoproteins and indicate that they are characteristically of high isoelectric point, with the exception of *L. peruvianum* $S_1$-gene protein, which has a pI of about 7.6.

A significant aspect of the present invention is the discovery that rabbit antisera and monoclonal antibodies raised to stylar extracts show that all the genotype-specific glycoproteins are antigenic and that they cross-react immunologically, indicating considerable structural homology between the products of the different S-alleles. Antibodies raised to all the S-gene proteins cross-react. Immunological cross-reactivity between these S-genotype-associated antigenic glycoproteins and extracts from styles of other self-incompatible crop and horticultural plants also indicates that the S-gene products in each case are highly conserved, that is they are closely related chemically. Specifically, the S-gene proteins hereof have the ability to immunologically cross-react with antibody to any of at least the S1-gene proteins of *Nicotiana alata*, the S2-gene protein of *Nicotiana alata*, the S3-gene gene protein of *Nicotiana alata*, the S1-gene protein of *Lycopersicon peruvianum*, the S2-gene protein of Lycopersicon peruvianum, the S3-gene protein of *Lycopersicon peruvianum*, the S7-gene protein of *Brassica oleracea*, the S7-gene protein of *Brassica campestris*, and the S-gene proteins of *Prunus avium*. Thus, there is structural homology among S-proteins and despite apparent differences in molecular weight and pI, these proteins are a recognizable structural class in addition to their functional similarities.

As a result of N-terminal sequencing, significant amino acid sequence homologies among S-proteins described herein were found, as shown in FIG. 14. N-terminal regions of six proteins were sequenced and shown to be homologous at positions 2 (Phe), 4 (Tyr), 6 (Gln), 7 (Leu), 8 (Val), 9 (Leu), 12 (Pro), and 15 (Phe), with additional homologies among selected protein pairs and triplets taken from the six proteins sequenced. In the region sequenced (amino acids 1-15), the *N. alata* $S_2$-protein is 80% homologous to the *N. alata* $S_6$-protein, 67% homologous to the *L. peruvianum* $S_1$-protein, and 53% homologous to the *L. peruvianum* $S_3$-protein. These homologies, which are characterized as greater than about 50%, provide a further identifying property of S-gene proteins as a class.

The protein purified from a plant extract as described herein, may be a modified protein from a plant extract, for example a deglycosylated or partially deglycosylated protein, or may be synthesized, for example by means known to the art or as a gene product as described in Ser. No. 854,139.

A method provided herein for preparing a purified S-gene protein associated with a self-incompatibility allele of a plant comprises:

(a) identifying a molecular weight range of S-gene proteins in which stylar extract proteins from different self-incompatibility genotypes vary;

(b) extracting with an aqueous buffer a homogenate of styles of said plant from a genotype thereof homozygous for self-incompatibility;

(c) fractionating the extract of step (b) by ion exchange chromatography on an anion exchanger eluted with a salt gradient;

(d) selecting a fraction from step (c) containing S-gene protein;

(e) fractionating genotype-specific protein-containing fractions from the fraction of step (d) by affinity chromatography on ConA cross-linked to a chromatographic support matrix and eluted with an alpha glycoside in aqueous solution; and (f) pooling S-gene protein containing chromatographic fractions derived from step (e) whereby S-gene protein in purified form is obtained.

Further details of these antigenic glycoprotein materials, and of their isolation and identification, are given in the following detailed description.

BRIEF DESCRIPTION OF THE DRAWINGS

FIGS. 1 and 2 illustrate pollen tube growth in compatible and incompatible pollinations, respectively. Both figures are photomicrographs of sections or style cut lengthwise, and stained with a pollen tube-specific fluorescent stain after pollination. In FIG. 1, the style expressing both $S_3$ and $S_4$ alleles were pollinated by compatible pollen expressing either $S_1$ of $S_2$ alleles. The pollen tubes grew directly to the ovary. In FIG. 2, the alleles of the pollen grains matched those in the style. Pollen growth was arrested in the upper part of the style.

FIG. 3 shows the results of partial 2-dimensional gel electrophoresis of whole stylar extracts of mature *L. peruvianum* genotypes $S_2S_2$, $S_2S_3$ and $S_1S_3$, and of *N. alata* genotypes $S_2S_2$, $S_2S_3$, $S_3S_3$ and $S_1S_3$, with the bands associated with the various S-genotypes identified, as revealed by silver stain and by Coomassie Blue stain.

FIG. 4 shows 2-dimensional gel electrophoretic separations of style extracts of *L. peruvianum* genotypes $S_1S_2$, $S_1S_3$, $S_2S_3$, $S_3S_3$, $S_3S_4$ and $S_2S_2$, with the bands associated with the various genotypes identified.

FIG. 6 shows the results of SDS-PAGE of whole stylar extracts of self-incompatible *N. alata* genotypes at various developmental stages where A is mature flowers, B is open but immature flowers, C in onset of petal coloration, D is elongated green bud, and E is green bud.

FIG. 7 shows DEAE-Sepharose chromatography of *Nicotiana alata* style extract; FIG. 8 shows Biogel P150 chromatography of $S_2$glycoprotein after DEAE-Sepharose chromatography; FIG. 9 shows ConA-Sepharose affinity chromatography of $S_2$-glycoprotein fraction after DEAE-Sepharose chromatography; and FIG. 10 shows Biogel P$\frac{1}{4}$chromatography of $S_2$-glycoprotein after chromatography on ConA- Sepharose.

1. Unfractionated style extract from *L. peruvianum* ($S_1S_3$).
2. Unfractionated style extract from *N. alata* ($S_1S_3$).
3. Purified S-glycoprotein from *Brassica compestris* ($S_7$), a gift from Dr. Hinata.
4. Purified S-glycoprotein from *Prunus avium* ($S_3S_4$).

FIG. 13 shows the immuno-precipitation of style extracts from *N. alata*, *P. avium* and *L. peruvianum* with purified rabbit antiserum against purified S-glycoprotein of P. avium.

FIG. 14 provides the N-terminal amino acid sequences of the mature N. alata $S_2$, $S_6$, $S_z$ and $S_{f11}$ proteins and the mature L. peruvianum $S_1$ and $S_3$ proteins. Amino acid homology is indicated by enclosures. Data comparing the pI and Mr values are also provided.

FIG. 15 provides the amino acid sequence as deduced from nucleotide sequence of the cDNA coding for the 32K molecular weight-$S_2$ protein of N. alata.

Figure 16:
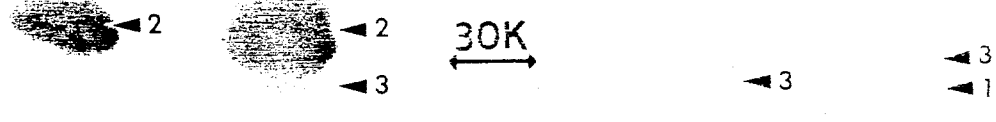

FIG. 16 shows western blots of style extracts of $S_1S_3$, $S_2S_3$, $S_2S_2$, and $S_3S_3$ genotypes using antiserum raised to unfractionated styles of genotype $S_1S_3$ (N. alata).

DESCRIPTION OF THE PREFERRED EMBODIMENT

The class of S-gene proteins claimed herein were shown in the following examples to have a number of characteristic properties.

Definition of S-genotypes of L. peruvianum. Seeds of an unselected line of L. peruvianum Mill. were obtained from the Victorian State Department of agriculture, Burnley, Victoria, Australia. Two vigorous, abundantly flowering plants were selected for analysis of the breeding system. These were hand self-pollinated to confirm self-incompatibility, and then crossed reciprocally to produce two groups of progeny. When the progeny were each crossed as females with pollen from their respective male parents, half of the pollinations were incompatible, indicating that the original parent plants had a common allele. Accordingly, the parent plants were assigned the genotypes $S_1S_2$ and $S_1S_3$, and progeny genotypes were confirmed by selected crosses from a diallele array involving parents and progeny. Clones were established from three vigorous progeny plants with the genotypes $S_1S_2$, $S_1S_3$ and $S_2S_3$. Self pollinations of these clones at the green-bud stage gave rise to homozygous plants $S_1S_1$, $S_2S_2$ and $S_3S_3$. An additional genotype bearing a fourth allele, $S_3S_4$, were obtained by crossing the $S_1S_3$ clone with an unrelated third plant from the original seed accession. Thus all clones in the analysis, with the exception of $S_3S_4$, are derived from only two original parent plants and carry an equal genetic contribution from both.

Sources of defined S-genotypes of Nicotiana alata. Nicotiana alata $S_6S_7$ was a gift of Dr. G. Breidemeijer, Stichting Ital., Wageningen, the Netherlands. Plants homozygous for the $S_6$-allele were generated by bud selfpollination. Nicotiana alata plants homozygous for the $S_{F11}$ and $S_z$ alleles were generated from original seeds provided by Dr. K. K. Pandey, Grasslands, Palmerston North, New Zealand, as described by Kheyr-Pour and Pernes (1985), "A new S-allele and specific S-protein associated with two S-alleles in Nicotiana alata", in Biotechnology and Ecology of Pollen, Mulcahy, D. L. and Ottaviano, E. (eds)., Springer-Verlag, New York Berlin Heidelberg, pp. 191 $\propto$ 196. The style proteins corresponding to the $S_2$- $S_6$, $S_{F11}$- and $S_z$-alleles were identified by gel electrophoresis using published information on the pI and relative molecular masses (Mr) of the individual proteins (A. Clarke et al. (1985) J. Cell. Sci. Supp. 2:261-285; G. Breidemeijer et al. (1981) Theor. Appl. Genet. 59:185-190; A. Kheyr-Pour et al. (1985) supra.

Bud pollination to produce homozygotes: Buds generated from N. alata or L. peruvianum heterozygous plants $S_2S_3$ and $S_1S_3$ at the elongated green bud (stage D, FIG. 6) were emasculated by carefully slitting the corolla with fine forceps and gently removing the immature anthers. Twenty-four hours after emasculation (just prior to petal coloration, between stages D and C, FIG. 6) the immature stigma was pollinated with self pollen from a mature dehisced anther of another flower. Prior to pollination the stigma surface was coated with either:

(i) Exudate from a mature stigma applied by gently touching the two together or (ii) 15% sucrose in 0.001% borate applied by carefully touching the stigma into a drop of this solution on a glass Petri dish.

After this treatment, the stigma was pollinated by gently touching it onto a glass Petri dish containing mature pollen or by brushing pollen carefully onto the stigma surface with a fine artist's brush. To prevent premature flower drop the flower axis was smeared with a little 1% (w/w) indole acetic (Sigma Cat. No. 1-1250) acid in raw lanoline using a flat ended spatula.

The bud-pollinated plants were kept in the Phytotron at 20° C. and constant humidity and were labelled with key-tags placed on the floral axis. After six weeks the mature, dry seed pods were harvested.

The genotype of the $F_1$ progeny was established by test crossing against testers of known self-incompatibility genotype.

The general methods used in the isolation and identification of the antigenic glycoprotein materials are as follows:

Collection and storage of Styles: Mature, unpollinated styles were collected 24 to 48 hours after emasculation of buds at the stage of petal coloration (stage C, FIG. 6). Styles used for antisera production were either used immediately after collection or freeze dried and stored desiccated at −20° C. Styles extracted for protein analysis (gels or purification) were either fresh or stored at −70° C. (Style is used here to refer to the style plus stigma.)

Preparation of extract for raising specific antisera: Styles were ground, using a mortar and pestle, in 50 mM Tris-HCl, pH 8.5 , 1 mM $CaCl_2$, 1 mM dithiothreitol (DTT), 10 mM NaCl, 3% (w/v) polyvinyl pyrrolidone (PVP) at 0° C. for 5 minutes. Approximately 400 styles (1 g freeze-dried styles or 4.5 g fresh styles) were used per 30 ml extraction buffer. The extract was centrifuged at 10,000 g for 15 minutes at 40° C.: the clear green supernatant was removed and stored in 1 ml aliquots at −20° C. Prior to injection of the rabbits, 1 ml of the supernatant was passed down a Sephadex G-25 column (1 cm×20 cm; Vo=5.8 ml) previously equilibriated with 0.005M sodium phosphate buffer, 0.15M sodium chloride, pH 7.4 (PBS).

Preparation of extract for gel electrophoresis and immunoblot assays: Styles were snap frozen in liquid nitrogen and ground to a fine powder using a mortar and pestle. This powder was extracted in 50 mM Tris-HCl, pH 8.5, 1 mM DTT, 10 mM NaCl, 10 mM EDTA, 1 mM phenylmethylsulfonyl fluoride (PMSF), 1% (w/v) PVP at 0° C. for 5 minutes. (100 styles per 10 ml extraction buffer). The extract was centrifuged at 10,000 g for 10 minutes at 4° C.; the supernatant was removed and stored at −20° C. in 1 ml aliquots. Protein concentration of the extracts was determined as bovine serum albumin (BSA) using the Biorad protein assay kit (Biorad Laboratories, Inc., Richmond, Calif.).

Preparation of antisera: Antisera to crude stylar extracts of N. alata were raised in rabbits by inoculation with 1 mg of protein antigen in 0.5 ml in Freund's complete adjuvant (1.5 ml) administered either by multiple subcutaneous injections behind the neck or in a single dose intramuscularly in the flank. The rabbits were re-inoculated 6 weeks later with a further 1 mg of antigen in Freund's incomplete adjuvant. After 7 to 10 days the rabbits were bled from the marginal ear vein, the sera collected and stored at −70° C. in 200 μl aliquots.

Immuno absorption of specific antisera: Immuno absorption was carried out by a single incubation of antiserum with freeze-dried styles (15 styles per 1 ml antiserum) for 0.5, 1, 1.5, 2 or 2.5 hours at 20° C. The styles were removed and the antiserum centrifuged at 10,000 g for 10 minutes at 4° C. to remove any remaining debris.

Polyacrylamide gel electrophoresis: Sodium dodecyl sulphate polyacrylamide gel electrophoresis (SDS-PAGE) was performed according to Laemli, U. K., Favre, M. (1973) J. Mol. Biol. 80:575–583 using 12.5% (w/v) acrylamide. The samples were reduced by adding 1.43M 2-mercaptoethanol to the sample buffer and heating for 2 minutes in a boiling water bath. Molecular weight standards were phosphorylase B (94,000), bovine serum albumin (67,000), ovalbumin (43,000), carbonic anhydrase (30,000), soybean trypsin inhibitor (20,100) and B-lactalbumin (14,400) for Coomassie Blue staining and [$^{14}$C]methylated myosin (200,000), phosphorylase B (92,000), BSA (69,000), ovalbumin (46,000), carbonic anhydrase (30,000) and lysozyme (14,300) for electrophoretic blotting.

Electrophoresis was at 25 mA per gel for the stacking gel and 40 mA per gel for the running gel. After electrophoresis the gels were either stained with 0.14% (w/v) Coomassie Blue in 45% (v/v) methanol, 9% (v/v) acetic acid or were transferred to nitrocellulose paper.

Electrophoretic blotting: After electrophoretic separation of the proteins (20 μg) in a polyacrylamide gel, the proteins were transferred and bound to nitrocellulose paper in an electrophoretic blot apparatus (Biorad Laboratories, Richmond, Calif., USA) by electrophoresis at 0.1 A for 12 hours, at 20° C. in 20 mM Tris-HCl, 20% methanol, 15 mM glycine, pH 8.3.

Partial 2-dimensional gel electrophoresis

Style extracts of *L. peruvianum* were prepared by lightly crushing six styles with a fine glass rod in the presence of 20 μl of extraction buffer (0.1M Tris-HCl pH8.5, 10 mM EDTA, 0.1M NaCl, 1 mM CaCl$_2$). The extract was centrifuged at 10,000 g for 15 minutes at 4° C. and the supernatant was collected and examined by two dimensional gel electrophoresis.

Extract (15 μl containing approximately 15 μg protein) was applied to an LKB Ampholine PAG plate, LKB-Produkter AB, Bromma, SWeden (24 cm wide, 10 cm long) containing ampholine (pH3.5–9.5). Isoelectric focussing was performed according to the Manufacturer's instructions with the following modifications: constant power (15 watts) at 10° C. for 3.6 hours with 9 cm between the electrodes. Electrode solutions were 1M NaOH (cathode) and 1M H$_3$PO$_4$ (anode). The gel was fixed with 10% TCA and 35% sulphosalicyclic acid for 30 minutes prior to staining with Coomassie Brilliant Blue.

Figure 5:
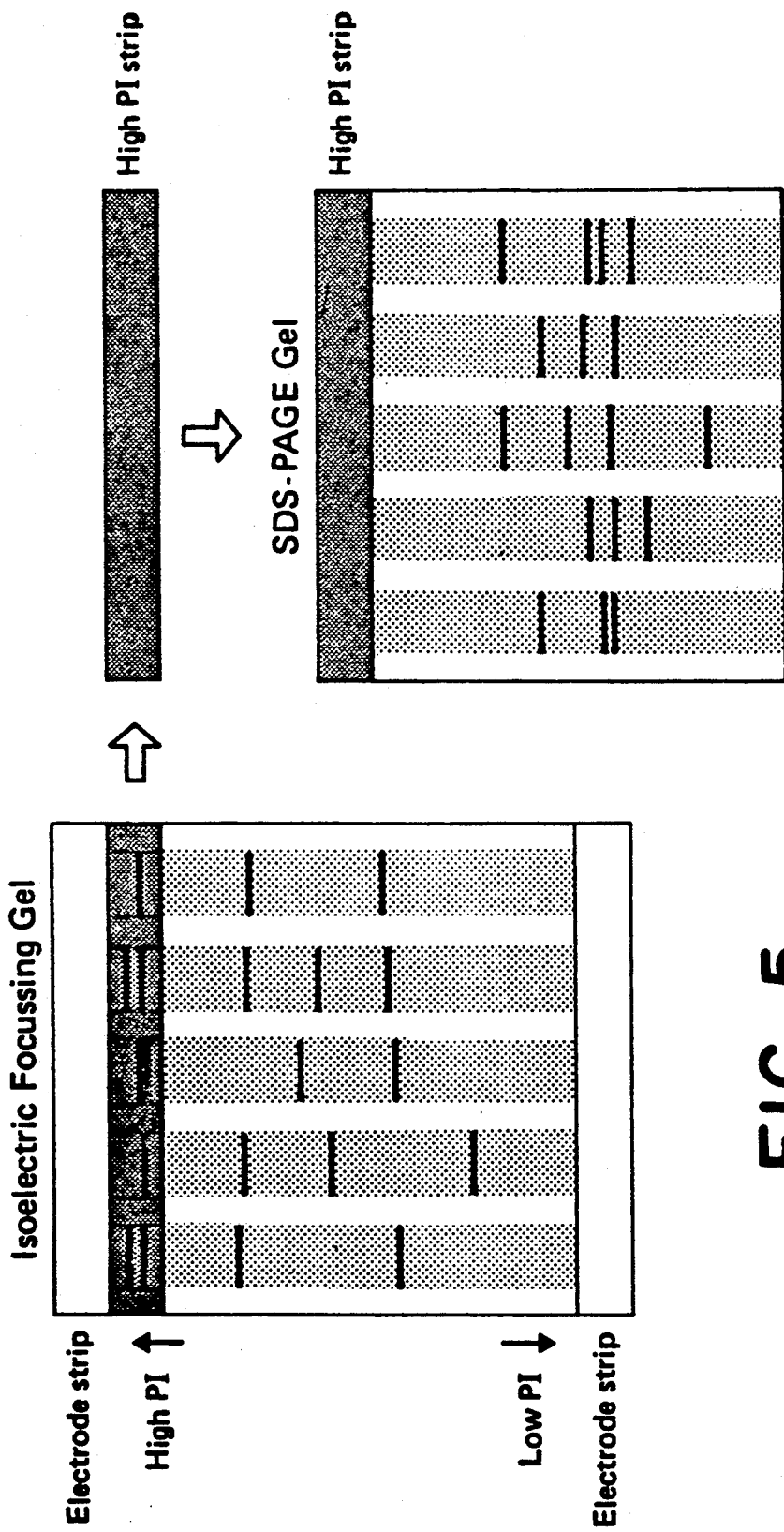
FIG. 5 shows diagramatically the partial 2-dimensional gel electrophoresis procedure described herein.

The protein track (approximately 0.5 cm) or in some instances, proteins from a selected narrow pI range, from the isoelectric focussing gel was cut out and placed in 200 ml of distilled water for 10 minutes, then transferred to 10 ml of 1M Tris-HCl pH6.8 for 5 minutes. The gel strips were further rinsed with distilled water for 10 minutes before being equilibrated with SDS sample buffer for 1.5 hours at room temperature and placed on the top of an SDS-polyacrylamide gel as shown in FIG. 5. The second dimensional gel electrophoresis was carried out according to Laemmli et al. (1973) using 15% acrylamide. The protein was detected by staining with silver reagent or Coomassie blue.

Immuno-blot assays: After the proteins had been electrophoretically transferred to nitrocellulose paper, the remaining active sites on the paper were blocked by washing the paper in 3% (w/v) BSA in 10 mM Tris-HCl, pH 7.4, 0.9% (w/v) NaCl, with gentle agitation for 1 hour at 20° C. Before addition of antiserum, the paper was rinsed in 10 mM Tris-HCl, 0.9% (w/v) NaCl, pH 7.4 (Tris-saline) for 0.5 hour at 20° C. The antiserum was diluted 1 in 25, 1 in 100, or 1 in 200 with 3% (w/v) BSA in Tris-saline and incubated with the nitrocellulose paper for 1.5 hours at 20° C. with gentle agitation. The nitrocellulose paper was washed for 10 minutes at 20° C. in Tris-saline, followed by 10 minutes at 20° C. in 0.05% (v/v) NP-40 (Trademark, Particle Data Labs. Elmhurst, Ill.) in Tris-saline, and then 10 minutes at 20° C. in Trissaline.

Protein A (40 μg) was labelled with $^{125}$I; 0.3 mCi using the Iodogen method (specific activity $1 \times 10^4$ to $1 \times 10^5$ cpm per μg Protein A). $^{125}$I-Protein A (20 μg) was diluted to 200 ml in 3% BSA in Tris-saline and incubated with the nitrocellulose paper for 0.5 hours with gentle agitation at 20° C. The nitrocellulose paper was washed in Tris-saline, then 0.05% NP-40 in Trissaline for 10 minutes each at 20° C. The final wash was in Tris-saline containing 0.5% Triton X-100 (Trademark, Rohm and Haas Corp., Philadelphia, Pa.), 0.1% SDS, 0.25% gelatine and 5 mM EDTA for 1 hour at 20° C. with gentle agitation. The paper was sealed in a plastic bag and exposed to Kodak XAR-5 x-ray film (Eastman Kodak Co., Rochester, N.Y.), for 6–16 hours at −70° C.

Immunoprecipitation conditions: 70 μl of buffer (Tris-HCl, pH 7.4, 50 mM; NaCl, 0.4M; EDTA, 5 nM, KI, 5 mM; NP-40, 0.05%; PMSF, 1 mM), 20 μl of iodinated extract (containing $1 \rightarrow 10 \times 10^6$ CPM), 5μl of ascites fluid or 10 μl of nonimmune mouse serum or 10 μl of rabbit anti-style serum were mixed and incubated at 4° C. for 1 hour. After this period, 10 μl of anti-mouse IgG (anti-mouse IgG –Sigma M8890) was added and the mixture incubated for a further hour at 4° C. A suspension of *Staph. aureus* cells (20 μl) was then added and the mixture centrifuged (10,000 g; 5 minutes). The pellet was washed three times in immunoprecipitation buffer and then incubated at 90° C. for 90 seconds with SDS-buffer (1×Laemmli sample) and the resulting solution examined by SDSPAGE using 12.5% buffer acrylamide.

Purification of 32K S$_2$-Glycoprotein from *Nicotiana alata* styles: Flowers from *N. alata* (genotype S$_2$S$_2$) were emasculated at the onset of petal coloration. Two days later, the fully mature styles were removed and stored at −70° C. (Styles refer to the style and stigma which were removed together; ovary is not included.) Frozen styles (3 g) were ground to a fine powder in liquid nitrogen using a mortar and pestle; this was followed by further grinding in 50 ml of extracting buffer (50 mm Tris-HCl, pH 8.5, 1 mM CaCl$_2$, 10 mM NaCl, 1 mM DTT, 10 mM EDTA and 1% (w/w) insoluble polyvinylpyrollidone. The homogenate was centrifuged (12,000 g; 15 minutes) and the supernatant (11 ml) was collected.

Figure 7:
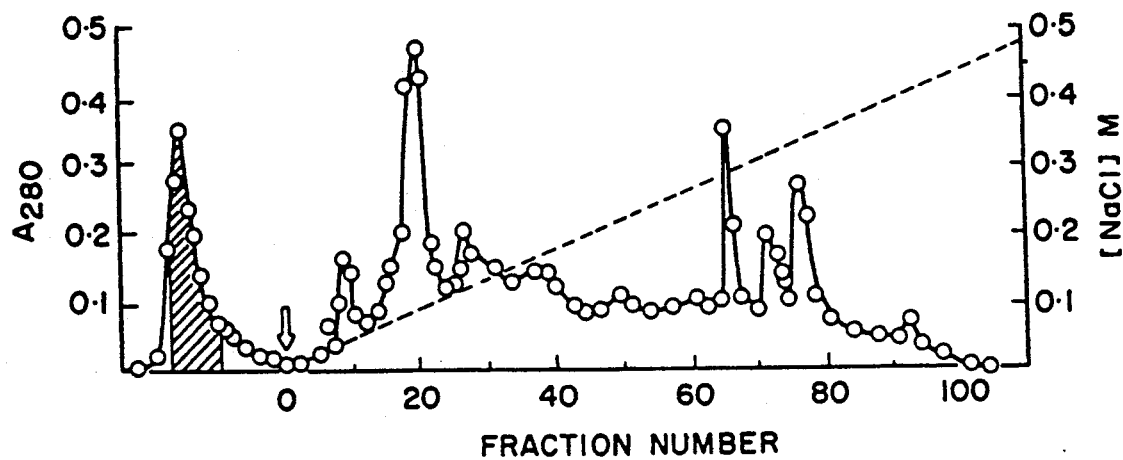
FIGS. 7-10 show stages of the purification of the 32 kd S-gene protein of *N. alata*, genotype $S_2$ on ion-exchange chromatography, followed by gel filtration or affinity banding and gel filtration where
Figure 8:
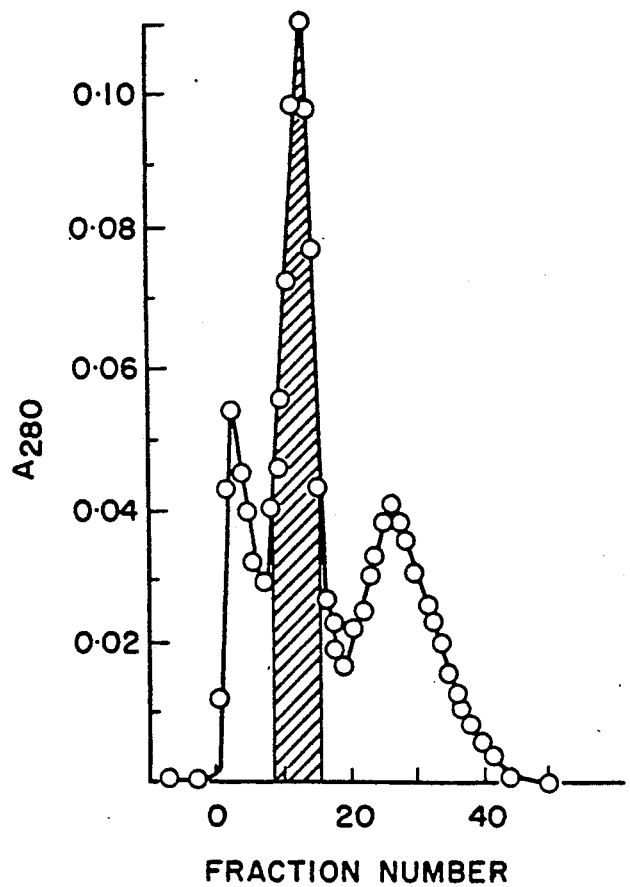
Figure 9:
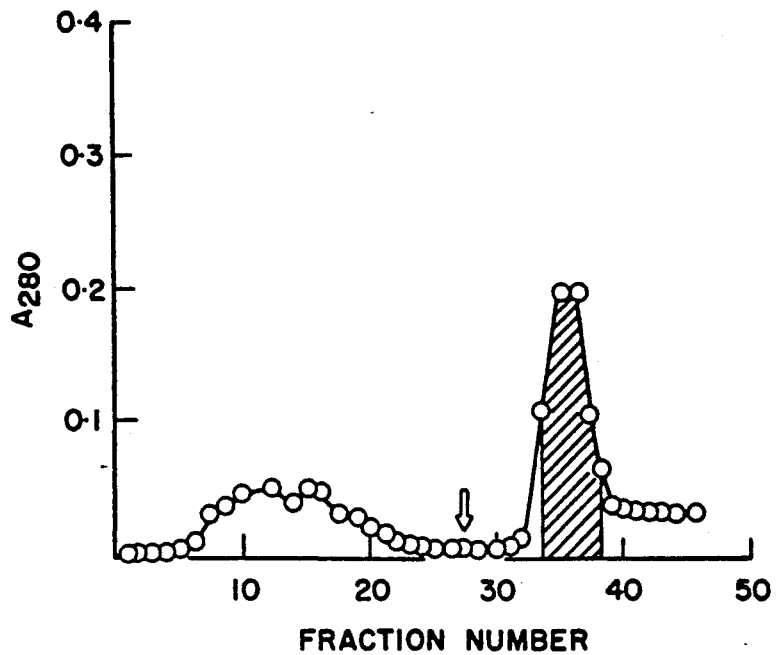
Figure 10:
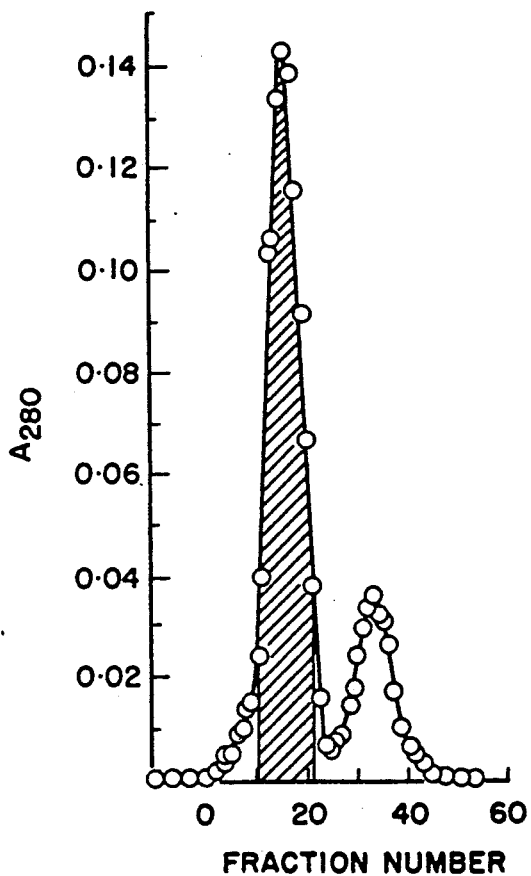

Prior to ion exchange chromatography the style extract (11 ml) was equilibrated with NH$_4$HCO$_3$ 5 mM pH 8.6, NaCl 1 mM, CaCl$_2$, 1 mM, EDTA 1 mM by passage through a Sephadex G-25 (Trademark, Pharmacia Inc., Uppsala, Sweden) column (1.6 cm diameter; 22 cm long, void volume 11 ml). The first 16 ml eluted after the void volume was collected and applied to DEAE-Sepharose (Trademark, Pharmacia Inc., Uppsala, Sweden) (Bed volume 26 ml, 1.6 cm diameter × 13 cm long) which was equilibrated with the same ammonium bicarbonate buffer. The column was then washed with this buffer (50 ml) before the application of a NaCl gradient (0-0.5M). The elution profile is shown in FIG. 7. Elution was monitored by A$_{280}$. Each fraction was examined by SDS-PAGE for the presence of the 32K S$_2$-glycoprotein. The S$_2$-glycoprotein was present in the unbound fractions (hatched area) which were combined as shown in FIG. 7 and concentrated to a final volume of 16 ml by rotary evaporation at room temperature. The S$_2$-glycoprotein was further purified by size fractionation on Biogel P150 (Trademark, BioRad Laboratories, Richmond, Calif.) (FIG. 8) or by affinity chromatography using ConA-Sepharose (Trademark, Pharmacia Inc., Uppsala, Sweden) followed by gel filtrations on Bio gel P-150 (FIGS. 9 and 10).

The unbound fraction from DEAE-Sepharose (8 ml) was applied to a column of Biogel P150 (void volume 14 ml; 1.6 cm in diameter, 36.5 cm long) which was equilibrated with NH$_4$HCO$_3$ 10 mM, pH 8.5, EDTA 10 mM, NaCl 0.1M, CaCl$_2$ 1 mM. The elution profile is shown in FIG. 8. Fractions were examined for the presence of the 32K S$_2$-glycoprotein by SDS-PAGE. The fractions containing the S$_2$-glycoprotein (Fractions 9-16) were combined and concentrated to 1 ml by rotary evaporation.

ConA-Sepharose was washed with 5 volumes of methyl-α-D-mannoside (0.1M) in buffer (sodium acetate 20 mM, pH 7.8; NaCl 0.1M, MgCl$_2$ 1 mM, CaCl$_2$ 1 mM, MnCl$_2$ 1 mM). The washed ConA-Sepharose was then transferred to bicarbonate buffer (0.25M NaHCO$_3$ pH 8.8) for 1 hour at room temperature; the bicarbonate buffer was changed 4 times during the 1 hour period. Four volumes of NaHCO$_3$ 0.25M, pH 8.8 containing 0.03% (v/v) glutaraldehyde were added and the ConA-Sepharose was then washed with NaHCO$_3$ 0.1M, pH 8.0, containing 0.5M NaCl, resuspended in acetate buffer (sodium acetate 10 mM, pH 7.8; NaCl 0.1M, MgCl$_2$ 1 mM; CaCl$_2$ 1 mM, MnCl$_2$ 1 mM and packed into a column (0.8 cm diameter, 14 cm long). In a repeat of this process, the pH of the acetate buffer was lowered to 7 with improved yields, as the protein appears to be more stable at lower pH. The unbound fraction from DEAE-Sepharose was equilibrated in acetate buffer, by passing through a G25-Sephadex column equilibrated with acetate buffer, then applied to the column. Unbound material was collected, the column washed with 10 volumes of acetate buffer, and the bound material eluted with 0.1M methyl-α-D-mannoside in acetate buffer. The profile is shown in FIG. 9. Fractions 34-38 were collected and concentrated to 1 ml by rotary evaporation The pooled fraction eluted by 0.1M methyl-α-D-mannoside was applied to a column of Biogel P150 to separate the methyl-α-D-mannoside from the S$_2$-glycoprotein (FIG. 10) (void volume 13 ml, 1.6 cm diameter; 36.5 cm long equilibrated and run in NH$_4$HCO$_3$ 10 mM pH 8.5, EDTA 10 mM, NaCl 0.1M CaCl$_2$ 1 mM). A further passage through Biogel P2 in water, to remove any trace of methyl-α-D-mannoside, was used before undertaking carbohydrate analysis of the S$_2$-glycoprotein.

| Recovery of protein applied | mg protein | % recovery | |
|---|---|---|---|
| Style extract recovered from Sephadex G-25 chromatography | 28.6 | | |
| Fraction not bound to DEAE-Sepharose | 2.79 | 9.7 | |
| Biogel P150 (Fractions 9-16) | 0.56 | 2.0 | 3.7 |
| ConA-Sepharose (Fractions 34-38) | 0.49 | 1.7 | |

The purified S-gene protein was essentially homogenous by the criteria of SDS-PAGE and two-dimensional gel electrophoresis using either silver stain or Coomassie Blue stain to visualize the bands. SDS-PAGE was performed according to Laemli, U.K. and Favre, M. (1973) J. Mol. Biol. 80:575-583, using 12.5% (w/v) acrylamide. Samples were reduced in 1.43M 2 mercaptoethanol in sample buffer with heating for 2 minutes in a boiling water bath. After electrophoresis, gels were stained with Coomassie Blue. N-terminal sequence analysis showed that the purified material has less than 5% contamination with other proteins. The foregoing purification scheme is applicable, with such modifications as may be deemed appropriate to those of ordinary skill in the art, to the purification of other S-gene proteins, from other plant sources. The purification scheme yields S-gene- protein in substantially purified form. In a further experiment, style extracts were purified and N-terminal sequencing performed as follows:

Purification and amino-terminal sequencing of style proteins. Styles (0.175 g; 250 for *L. peruvianum* ; 20 for *N. alata* ) were ground in extraction buffer (0.4 ml). The extract was centrifuges (12,000 rpm; 15 min; 4° C.) and loaded on a continuous wick along the width of the isoelectric-focussing gel. The gel was run and protein-containing bands (0.5 cm wide) were excised after staining with Coomassie blue. The individual bands were loaded and run on separate SDS-polyacrylamide gels (15% polyacrylamide). The gels were stained for 5 minutes in Coomassie blue (0.1% in 40% methanol. 10% acetic acid; high-performance liquid chromatography (HPLC) grade methanol, analytical grade acetic acid) and destained in 40% methanol, 10% acetic acid. A band of equivalent area in which there was not protein was excised for control analyses. The excised bands were separately eluted by electrophoresis in 50 mM ammonium bicarbonate containing 0.1% SDS in small volumes, typically 120-200 μl (Stearne et al. (1985), J. Immunol. 134:443-448).

The electroeluted proteins (yield 10 μg) were loaded directly onto an ODS-ypersil reversed-phase HPLC microbore column (5 μm particle size; 100 mm length, 2.1 mm internal diameter; Hewlett Packard, Waldbronn, FRG) equilibrated in 90% n-propanol-10% water. The column was developed with a linear 10-min.

gradient from 90% n-propanol-10% water to 40% n-propanol-60% water containing 0.1% (v/v) trifluoroacetic acid. Flow rate was 100 μl.min$^{-1}$; column temperature was 20° C. A Perkin-Elmer (Norwalk, Conn., USA) HPLC system (model LC4) equipped with a model LC95 ultraviolet detector, a model LS4 fluorimeter and a model LSI 100 integrator was used. The column eluent was monitored for ultraviolet absorption at 278 nm and fluorescence (280 nm excitation, 360 nm emission). Fractions were collected manually. Automated sequence analyses were performed using a gas-phase sequencer (Applied Biosystems, Foster City, Calif., USA; Model 470A) and phenylthiohydantoin (PTH) amino acids were analysed by HPLC as described by B. Grego et al. (1985) (Eur. J. Biochem. 148:485-491. Aliquots (67%) from each cycle were analysed for PTH amino acid content and the yields were normalized to 100% injection. The HPLC peak heights were converted to picomoles for each derivative using values from a standard mixture of PTH amino acids. The average repetitive cycle yield at each cycle was calculated from the slope of the linear-least-squares fitted straight line. Amino-acid sequences are fiven in one-letter symbols (IUPACIUB IUB Commission on Biochemical Nomenclature 1968).

Figure 3:
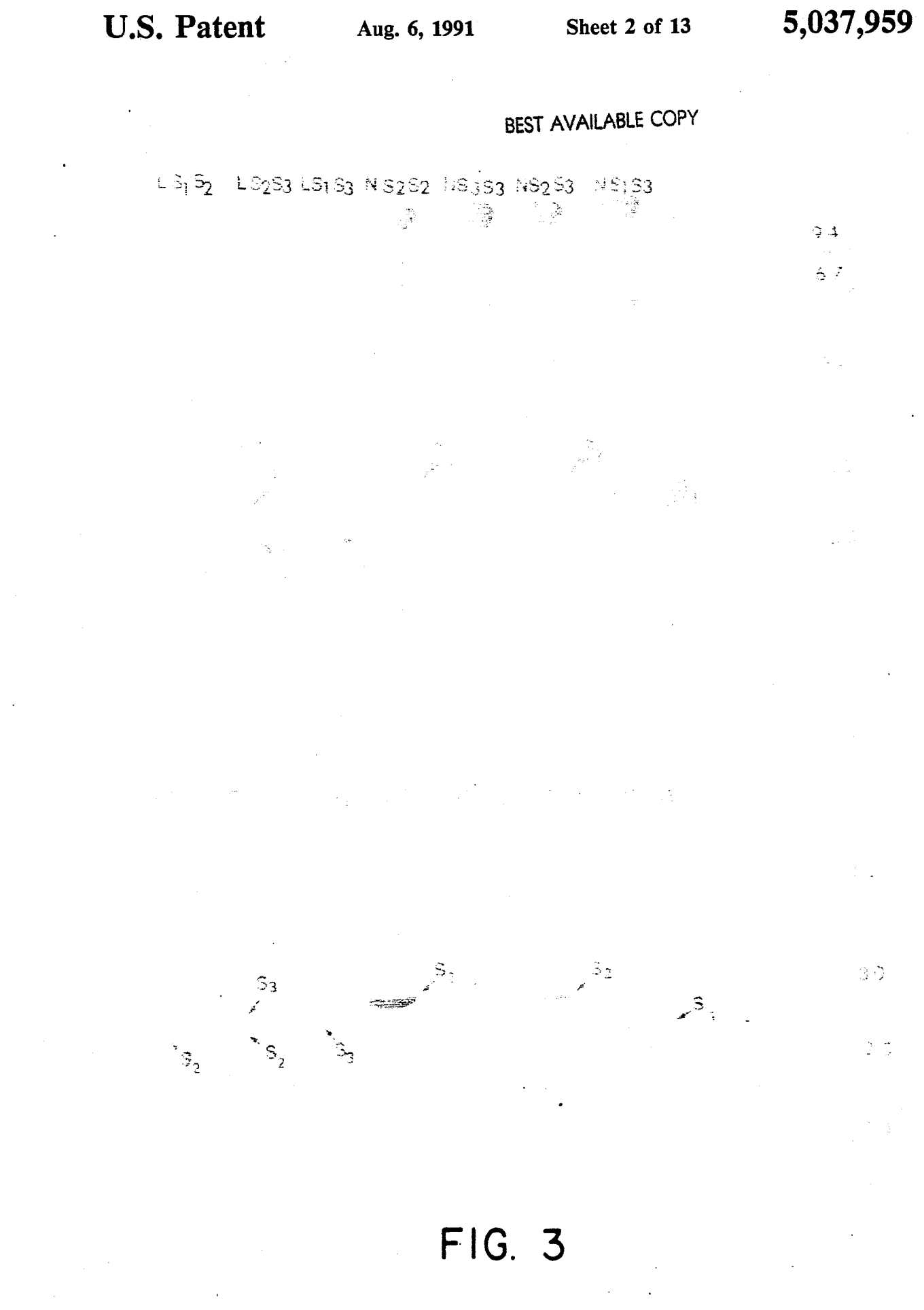

Partial 2-dimensional gel electrophoresis of whole stylar extracts: $N.$ $alata$ $S_1S_3$, $S_2S_3$, $S_2S_2$, and $S_3S_3$, and $L.$ $peruvianum$ $S_1S_2$, $S_2S_3$, $S_1S_3$, $S_2S_2$ and $S_3S_3$ showed a complex pattern of proteins in the MW range 20K to 120K. Most bands are common to all genotypes, but there are differences in the 20K-30K region which can be associated with S-genotype. These differences are apparent in the gels after staining with silver stain (FIG. 3, upper part) and with Coomassie blue (FIG. 3, lower part). Each lane in FIG. 3 is designated by genus initial (L=Lycopersicon, N=Nicotiana) and self-incompatibility genotype. Molecular weight markers are shown on the extreme right of each gel set.

The molecular weights of the S-gene proteins associated with each $N$ $alata$ genotype are approximately 27 kilodaltons (K) for $S_1$, and 32K for $S_2$, as determined with molecular weight markers. The $S_3$-gene product appeared to migrate at about 23K; however the simultaneous presence of a common band has made unequivocal designation difficult. S-gene specific proteins in the 23K-35K molecular weight range were consistently observed to be characteristic of their corresponding S-allele and to fit all the criteria described herein for S-gene proteins. Purified $N.$ $alata$ $S_2$-gene protein migrated as a single component on both SDS-PAGE and two-dimensional gels, as revealed either by Coomassie Blue or by silver stain. $L.$ $peruvianum$ styles yielded genotypespecific protein bands with molecular weights of approximately 25K-28K for each of $S_1$, $S_2$ and $S_3$-gene proteins. The proteins were further shown to be S-gene specific by 2-dimensional gel electrophoresis and by other criteria, as disclosed, infra.

2-dimensional gel electrophoresis of whole stylar extracts of mature $L.$ $peruvianum$ genotype: Distinct proteins were similarly observed in style extracts of $S_1S_3$, $S_1S_2$, $S_2S_3$, $S_3S_3$, $S_3S_4$ and $S_2S_2$ (FIG. 4). Molecular weights of $S_1$-, $S_2$- and $S_3$-gene proteins were all approximately 28K. $S_1$-gene protein had a lower pI than did $S_2$, $S_3$ and $S_4$. Two-dimensional gel electrophoresis was performed essentially as described by O'Farrell, et al. (1977) Cell 12:1133. The proteins fall into a major group of pI>7.5 and a minor group of low pI. The S-gene-proteins were found in the high pI group. In addition to the genotype-associated bands, designated in FIG. 4, there were two distinct bands at pI>9.5 common to all style extracts, running close to the genotype associated bands but distinguished from them by their higher molecular weight. Other bands in the lower pI range were found to differ from one extract to another, but no association of these bands with a particular genotype could be assigned.

Stylar proteins associated with style maturation: Extracts of $N.$ $alata$ $S_1S_3$ and $S_2S_3$ styles from the developmental stages of green bud, elongated bud, buds at first show of petal color, open but immature flowers and mature flowers with glistening styles, were prepared and subjected to SDS-PAGE (FIG. 6–this figure also illustrates the various developmental stages). A number of proteins were detected in all extracts of which those tentatively identified as the S-gene proteins in the 30K MW region, were present in extracts of buds at first show of petal color and in subsequent stages of maturation, but not in the earlier bud stages. The appearance of the bands tentatively assigned to S-genotype is summarized in Table 1. Similar results were observed for the S-gene proteins of $L.$ $peruvianum$. In one experiment, $S_2$ and $S_3$ gene proteins were present only in very low concentrations in extracts of green buds. There was a progressive increase in the apparent concentration of these components in extracts of styles taken from yellow buds and mature flowers. These results further confirm the identity of the described proteins as S-gene proteins according to the criteria set forth herein.

TABLE 1

Appearance of proteins corresponding to S-genotype in extracts of
Nicotiana alata ($S_1S_3$ and $S_2S_3$) styles
at different stages of maturity.
Presence of putative
S-gene product

| Developmental Stage | Genotype $S_1S_3$ | | Genotype $S_2S_3$ | |
| --- | --- | --- | --- | --- |
|  | $S_1$ | $S_3$ | $S_2$ | $S_3$ |
| Δ early bud | − | − | − | − |
| Δ elongated bud | − | − | − | − |
| * buds at first show of petal color | + | + | + | + |
| * open, immature flowers | + | + | + | + |
| * mature, flowers | + | + | + | + |

Δ Incompatibility not expressed - bud self-pollinations are successful.
* Incompatibility expressed - self-pollinations not successful.

Further studies demonstrating identity of $N.$ $alata$ 32K protein as $S_2$-gene protein: The 32K glycoprotein is present in the stigma and in the upper style sections in higher concentrations than in the lower sections of the style, as revealed by SDS-PAGE of extracts of 5 mm style sections. The highest concentration of the 32K glycoprotein was found in the upper part of the style, which is also the zone in which pollen tube inhibition occurs. Similarly, in $L.$ $peruvianum$, the $S_2$ and $S_3$ gene proteins were present in relatively high concentrations in the first segment containing the stigma and the top of the style and the next style segment (2 mm segments). The apparent concentration of these components decreased progressively in segments of the style taken towards the ovary, and none were detected in the ovary itself.

No bands corresponding to the $N.$ $alata$ 32K band were found in style extracts of $N.$ $tabaccum$, $N.$ $silvestris$, $N.$ $glauca$, or $Petunia$ $hybrida$ on SDS-PAGE. No bands corresponding to the 32K style band was found in extracts of other $N.$ $alata$ tissues, including petal, leaf, ovary and anther. The 32K band is therefore not a protein common to other species or to other *N. alata* tissues.

Biological activity of 32K $S_2$-gene protein was demonstrated in the in vitro pollen tube growth assay described by Williams, et al. (1982). $S_2$-gene protein at 25 μg/ml inhibited the growth of pollen tubes by about 70% provided the extraction buffer did not contain EDTA or other divalent ion binding agent. The results demonstrated that a biologically effective concentration of S-gene protein can act to inhibit pollen tube growth.

While the foregoing experiments have been carried out in greatest detail using the $S_2$, $S_6$, $S_z$ and $S_{F11}$-gene proteins of *N. alata* and $S_1$ and $S_3$ of *L. peruvianum* it will be apparent to those ordinarily skilled in the art that the similarities in timing of developmental expression, physical properties, association with self-incompatibility genotype and immunological properties taken together demonstrate that other S-gene proteins as described herein have been identified from a variety of plant species. As a result of the findings and teachings herein disclosed, S-gene proteins of self-incompatible species can now be identified, isolated, purified and characterized for use in plant breeding. Significant properties of S-gene proteins, demonstrating their fundamental structural similarity across species boundaries, are next demonstrated.

Figure 11:
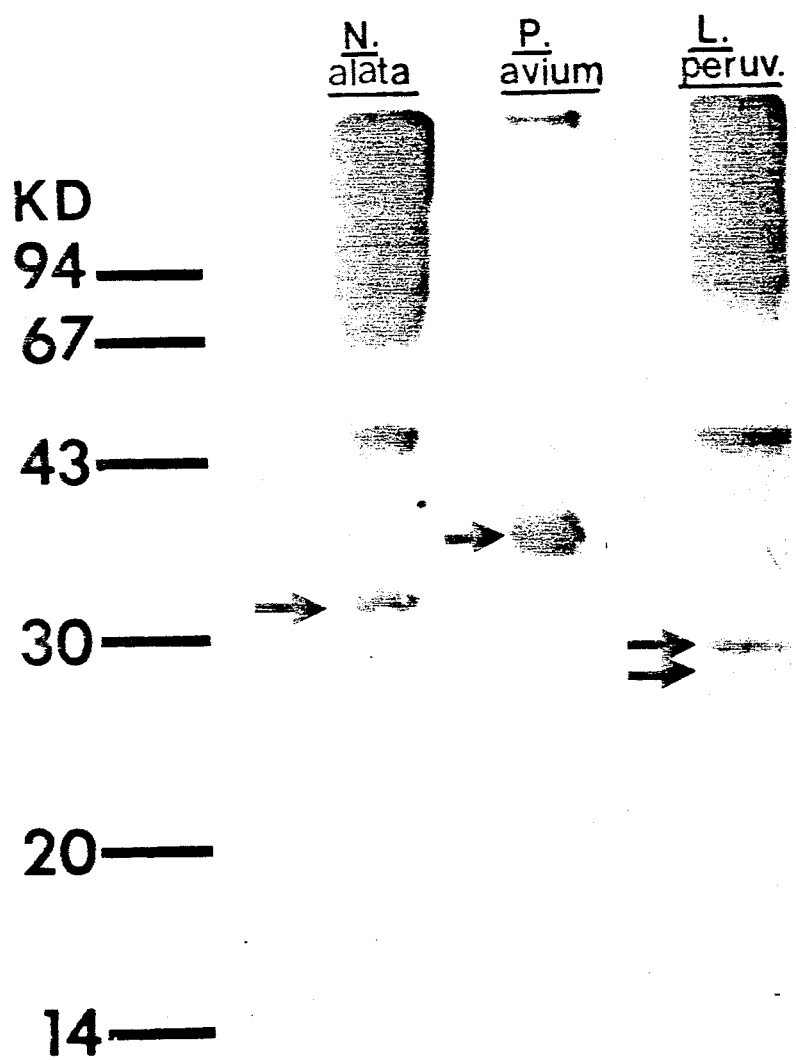
FIG. 11 Immunoprecipitation of $^{125}$I-labelled style extracts from *Nicotiana alata*, *Prunus avium* and *Lycopersicon peruvianum* with an antiserum raised in rabbits against the purified S-glycoprotein of *Prunus avium*. The antiserum was partially purified by affinity chromatography on Protein A-Sepharose.

Immunological cross-reactivity of S-gene protein from different plants: An antiserum was raised in rabbits against the S-protein of *Prunus avium*, purified as described by Mau, et al. (1982) supra. Style extracts from *N. alata*, *P. avium* and *L. peruvianum* were labeled with $^{125}I$ by the Iodogen technique of Fraker and Speck (1978) Biochem. Biophys. Res. Comm. 80:849. Labeled extracts were immunoprecipitated following the procedure detailed, supra. The anti-*P. avium* S-protein serum precipitated the 32K $S_2$-protein of *N. alata* and the S-proteins of approximately 28K of *L. peruvianum* (which revealed two bands since the source plant carried two S-alleles) in addition to *P. avium* S-protein (37K), as shown in FIG. 11.

Figure 12:
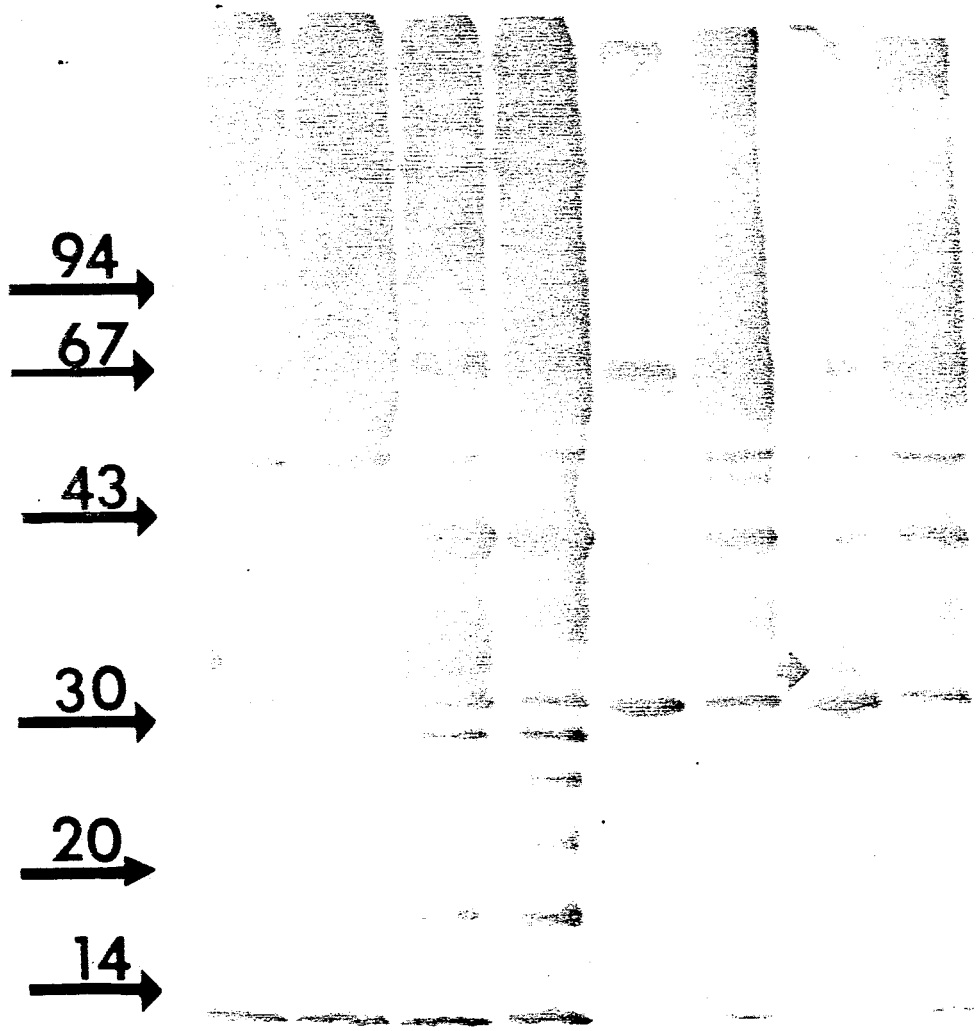
FIG. 12 Immunoprecipitation of $^{125}$I-labelled *N. alata* style extracts of $S_2S_3$ (A) and $S_3S_3$ (B) genotype with antiserum raised in rabbits against.

Using essentially the same technique, a variety of antisera were shown to immuno-precipitate $^{125}I$-labeled *N. alata* style extracts of genotypes $S_2S_3$ and $S_3S_3$. The results are shown in FIG. 12. Lanes A and B in each pair represent geotypes $S_2S_3$(A) and $S_3S_3$(B). Each numbered lane pair shows immunoprecipitation with a rabbit antiserum against: 1) *L. peruvianum* $S_1S_3$ unfractionated style extract; 2) *N. alata* $S_1S_3$ unfractionated style extract; 3) *Brassica campestris* $S_7$ partially purified S-glycoprotein [prepared and provided by K. Hinata, see Nishio and Hinata (1982)]; 4) *P. avium* $S_3S_4$ purified S-glycoprotein. The positions of molecular weight markers are shown on the left margin. Arrows show the position of 32K $S_2$-protein of *N. alata*. The $S_2$-glycoprotein was immunoprecipitated by heterologous antisera in each instance with the apparent exception of $S_2$ treated with anti-Brassica serum. However, as shown in FIG. 12, *N. alata* $S_2$-protein was precipitable by anti-Brassica serum.

In FIG. 13, the results of immunoprecipitation analysis using antiserum raised to *Brassica campestris* partially purified S-protein (provided by K. Hinata) are shown. The serum was able to immunoprecipitate S-protein in style extracts from *N. alata*, *P. avium*, and *L. peruvianum*, as marked by the arrows in the respective lanes of FIG. 13. Molecular weight marker positions in FIG. 13 are shown in the left hand margin.

Antigenic properties of stylar extracts: Antiserum to both *N. alata* $S_2S_3$ and $S_2S_3$ whole-stylar extract bound to proteins of stylar extracts of four *N. alata* genotypes analysis, the only detectable differences in binding patterns occurring in the 30K MW region. The pattern of antiserum binding is such that an association of a particular band with S-genotype can be assigned (FIG. 16). Normal rabbit serum did not bind to any of the extracts examined. A number of high MW proteins also reacted with the antiserum, but these were common to style extracts of all genotypes.

The fact of immunological cross-reactivity between S-proteins of different genotype within the same species, between S-proteins of different species and even between species having gametophytic incompatibility (Nicotiana, Lycopersicon) and sporophytic incompatibility (Brassica) indicates that these S-proteins have at least a single common component with homologous structures. Despite apparent differences in molecular weight and pI, the evidence disclosed herein reveals the surprising fact that S-gene proteins are a recognizable structural class, in addition to having functional similarities.

Uses of S-gene proteins and antibodies to these proteins: The availability of S-gene proteins and antibodies against them makes a variety of new plant breeding strategies possible. The difficulty of producing selfed seed in self-incompatible, outbreeding crops makes it very difficult to develop and maintain homozygous elite lines. The difficulty can be overcome by the use of an anti S-protein serum, which, when applied to the stigma with appropriate timing, can render a normally self-incompatible plant temporarily self-compatible. Conversely, a normally self-compatible plant can be rendered temporarily self-incompatible, and thereby prevent self-fertilization, by using S-protein applied by suitable means, for example as a spray or coating on the stigma surface. (A self-incompatible plant will normally reject pollen of a self-fertile (Sf) plant).

New interspecific hybrids can be created by techniques that exploit S-gene proteins. For example, domestic tomato cultivars can be improved by genetic inputs, such as pathogen resistance, drought tolerance and the like, from related wild species. A self-fertile cultivar, used as the female parent, is rendered temporarily self-incompatible by application of an S-gene protein, preferably that of a close, self-incompatible relative, to the stigmas of the plant. Such a phenotypic modification is symbolized by $S_fS_f(S_1)$. Pollination by a self-incompatible parent bearing a desired trait, designated by * will result in F1 progeny carrying one self-incompatibility allele and the desired trait.

$S_fS_f(S_1) \times S_2S_2^* \rightarrow S_fS_2^*$

Such F1 progeny cannot self-pollinate and will not set seed unless treated to inactivate the S-protein, for example, by use of anti-$S_2$ serum. However, such F1 plants may be themselves useful if they are of a crop where only vegetative parts are harvested, e.g., Brassica. Furthermore, the F1 plants can be used as male parents for backcrossing to the original $S_fS_f$ parent. By recurrent backcrosses to the $S_fS_f$ parent, accompanied by selection for the * gene, an $S_fS_f^*$ cultivar carrying that gene can be developed.

The foregoing strategy can be extended to produce hybrid seed. In one such scheme, four parental varieties are employed:

| Variety 1 | Variety 2 | Variety 3 | Variety 4 |
| --- | --- | --- | --- |
| $S_fS_f$ | $S_2S_2^*$ | $S_fS_f$ | $S_1S_1^*$ |

Varieties 1 and 3 are rendered temporarily self-incompatible by treatment with an appropriate S-gene protein. For example, for a cross between Var. 1 and Var. 2, Var. 1 is treated with an $S_1$-gene protein, to render it self-incompatible but compatible with Var. 2. It will be understood that Var. 1 and Var. 3 may in fact be identical, if desired, although they will be rendered temporarily distinct phenotypically by the S-gene protein treatment. Varieties 2 and 4 may be naturally self-incompatible. However, in certain instances it will be preferred to introduce the self-incompatibility alleles especially for the purpose, using any available and appropriate genetic manipulation. In crosses

| Var.1 × Var. 2 | | Var. 3 × Var. 4 |
| --- | --- | --- |
| $S_fS_f(S_1) \times S_2S_2^*$ | and | $S_fS_f(s_2) \times S_1S_1^*$ | the F1 progeny will be $S_fS_2^*$ and $S_fS_1$, respectively. As before, such plants are self-incompatible. However, the two F1 types are cross-compatible and a mixture of seed of both types will yield plants which can fertilize each other and set seed to produce a crop. ($1S_1S_1:2S_1S_2:1S_fS_2$)

The S-gene proteins and antibodies thereto are also of use to plant breeders to determine the self-incompatibility alleles carried by a given plant cultivar. Heretofore, such determinations required laborious and time-consuming crossing experiments. In vitro pollen tube growth assays can be used in combination with purified S-gene proteins of each known S-allele to identify the S-genotype of a pollen sample. Alternatively, specific S-gene protein antibodies can be used to identify corresponding proteins in style extracts. Antibodies that are allele-specific are preferred for distinguishing various allelic S-gene proteins from one another. For a given plant species the test materials can be produced in the form of a kit comprising a set of S-gene proteins, plates for in vitro pollen tube growth and buffered media for promoting pollen tube growth. A test kit for measuring S-gene proteins immunochemically, either quantitatively or qualitatively, would comprise a set of antibodies appropriate to the plant species, together with means for identifying the binding of an S-gene protein with its antibody. Such means could include fluorescent-dye coupled antibody, or enzyme-conjugated antibody to permit detection by fluorescence of an antigen-antibody complex, or by activity of the antibody-enzyme conjugate, the latter assay system being generally known in the art as enzyme-linked immunoabsorbent assay (ELISA). Other immunoassay detection means may be used, as appropriate, in accordance with principles of operation well known to those of ordinary skill in the art. For field testing and routine lab analysis, an ELISA is preferred.

Those skilled in the art will appreciate that the invention described herein and the methods of isolation and identification specifically described are susceptible to variations and modifications other than as specifically described. It is to be understood that the invention includes all such variations and modifications which fall within its spirit and scope.

We claim:

1. A purified and isolated glycoprotein having a molecular weight of between about 20 kd and about 37 kd, as determined by sodium dodecyl sulphate polyacrylamide gel electrophoresis under reducing conditions said glycoprotein being obtained from a plant style of a gametophytically self-incompatible plant which is a member of the family Solanaceae, said glycoprotein segregating with a single self-incompatibility allele of said plant and having the ability to inhibit pollen tube growth in said plant only from pollen having the same self-incompatibility allele, and having an amino acid sequence at the N-terminal thereof selected from the group consisting of:
    (1) Asp-Phe-Asp-Tyr-Leu-Gln-Leu-Val-Leu-Gln-X-Pro-Arg-Ser-Phe;
    (2) Tyr-Phe-Glu-Tyr-Leu-Gln-Leu-Val-Leu-Gln-X-Pro-Thr-Thr-Phe;
    (3) Ala-Phe-Glu-Tyr-Met-Gln-Leu-Val-Leu-Thr-Tro-Pro-Ile-Thr-Phe;
    (4) Ala-Phe-Glu-Tyr-Met-Gln-Leu-Val-Leu-Gln-Trp-Pro-Thr-Ala-Phe;
and (5) sequences having greater than about 50% homology in the N-terminal end thereof to any of the four N-terminal sequences.

2. A purified glycoprotein of claim 1 having the ability to immunologically cross-react with antibody to any of the S1-gene protein of Nicotanana alata, the S2-gene protein of Nicotiana alata, the S3-gene protein of Nicotiana alata, the S1-gene protein of Lycopersicon peruvianum, the S2-gene protein of Lycopersicon peruvianum, the S3-gene protein of Lycopersicon peruvianum, the S7-gene protein of Brassica oleracea, the S7-gene protein of Brassica campestris, or an S-gene protein of Prunus avium.

3. A purified glycoprotein of claim 1 wherein the gametophytically self-incompatible plant is a member of the genus Nicotiana.

4. A purified glycoprotein of claim 1 selected from the group consisting of proteins comprising the self-incompatibility alleles S1, S2, S3, S6, Sz, and SF11 of Nicotiana alata and S1, S2, S3 and S4 of Lycopersicon peruvianum.

5. A purified and isolated glycoprotein having a molecular weight of between about 20 kd and about 37 kd, as determined by sodium dodecyl sulphate polyacrylamide gel electrophoresis under reducing conditions said glycoprotein being obtained from a plant style of a gametophytically selfincompatible plant which is a member of the genus Lycopersicon, said glycoprotein segregating with a single self-incompatibility allele of said plant and having the ability to inhibit pollen tube growth in said plant only from pollen having the same self-incompatibility allele, and having an amino acid sequence at the N-terminal thereof selected from the group consisting of:
    (1) Asp-Phe-Asp-Tyr-Leu-Gln-Leu-Val-Leu-Gln-Pro-Arg-Ser-Phe;
    (2) Tyr-Phe-Glu-Tyr-Leu-Gln-Leu-Val-Leu-Gln-Pro-Thr-Thr-Phe;
    (3) Ala-Phe-Glu-Tyr-Met-Gln-Leu-Val-Leu-Thr-Tro-Pro-Ile-Thr-Phe;
    (4) Ala-Phe-Glu-Tyr-Met-Gln-Leu-Val-Leu-Gln-Trp-Pro-Thr-Ala-Phe;
and (5) sequences having greater than about 50% homology in the N-terminal end thereof to any of the four N-terminal sequences.

* * * * *

UNITED STATES PATENT AND TRADEMARK OFFICE
CERTIFICATE OF CORRECTION

PATENT NO. : 5,037,959

DATED : August 6, 1991

INVENTOR(S) : Clarke et al.

It is certified that error appears in the above-identified patent and that said Letters Patent is hereby corrected as shown below:

At column 2, line 14, please rewrite "selfincompatibility" as --self-incompatibility--. At column 2, line 48 please rewrite "N. alata" as --<u>N. alata</u>--. At column 5, line 21, please rewrite "Lycopersicon peruvianum" as --<u>Lycopersicon peruvianum</u>--. At column 6, circa line 11, please rewrite "or" as --of--. At column 6, line 15, please rewrite "of" as --or--. At column 6, line 46, please rewrite "$S_2$glycoprotein" as --$S_2$-glycoprotein--. At column 6, bridging lines 49-50, please rewrite "Biogel P 1/8 chromatography" as --Biogel P150 chromatography--. At column 6, line 52, please rewrite "FIG. 11 Immunoprecipitation" as --FIG. 11 shows the immunoprecipitation--. At column 6, line 58, please rewrite "FIG. 12 Immunoprecipitation" as --FIG. 12 shows the immunoprecipitation--. At column 7, line 20, please replace the period with a colon. At column 7, line 39, please rewrite "were" as --was--. At column 7, line 45, please replace the period with a colon. At column 7, bridging lines 56-57, align line 56 with line 57 to remove the space between "and" and "Ottaviano". At column 7, line 58, please rewrite "191 α 196" as --191-196--. At column 9, line 17, please rewrite "Laemli" as --Laemmli--. At column 9, line 25, please rewrite "B-lactalbumin" as --ß-lactalbumin--. At column 9, line 60, please rewrite "sulphosalicyclic" as --sulphosalicylic--. At column 10, circa line 39, please rewrite "5nM" as --5mM--. At column 10, circa line 52, please rewrite "SDSPAGE" as --SDS-PAGE--. At column 10, line 66, please rewrite "polyvinylpyrollidone" as --polyvinylpyrrolidone--. At column 11, line 2, please insert a comma after "5mM". At column 11, line 34, please rewrite "Bio gel" as --Biogel--. At column 11, line 58, please rewrite "long)." as --long))._--. At column 12, line 7, please insert a comma after "10mM".

UNITED STATES PATENT AND TRADEMARK OFFICE
CERTIFICATE OF CORRECTION

PATENT NO. : 5,037,,959

DATED : August 6, 1991

INVENTOR(S) : Clarke et al

It is certified that error appears in the above-identified patent and that said Letters Patent is hereby corrected as shown below:

At column 12, line 8, please insert a comma after "NaCl 0.1M". At column 12, line 27, please rewrite "Laemli" as --Laemmli--. At column 12, line 45, please rewrite "centrifuges" as --centrifuged--. At column 12, line 57, please rewrite "not" as --no--. At column 13, line 15, please rewrite "(Eur." as --Eur.--. At column 13, line 23, please rewrite "fiven" as --given--. At page 13, line 24, please rewrite "IUPACIUBIUB" as --IUPAC-IUB--. At page 13, line 53, please rewrite "genotypespecific" as --genotype-specific--. At page 13, line 54, please rewrite "$S_1$, $S_2$" as --$S_1$-, $S_2$- --. At column 14, line 11, please rewrite "bud" as --buds-- (both occurrences). At column 15, circa line 45, please rewrite "geotype" as --genotype--. At column 15, line 58, please rewrite "Brassica" as --*Brassica*--. At column 15, line 59, please rewrite "FIG. 12" as --FIG. 13--. At column 16, line 2, please rewrite "$S_2S_3$", first occurrence, as --$S_1S_3$--. At column 16, line 3, please insert --in a Western blot-- after "genotypes". At column 16, line 16, please rewrite "Nicotiana, Lycopersicon" as --*Nicotiana, Lycopersicon*--. At column 16, line 17, please rewrite "Brassica" as --*Brassica*--. At column 16, line 60, please rewrite "Brassica" as --*Brassica*--. At column 17, circa line 53, please rewrite "antigenantibody" as --antigen antibody--.

UNITED STATES PATENT AND TRADEMARK OFFICE
CERTIFICATE OF CORRECTION

PATENT NO. : 5,037,959

DATED : August 6, 1991

Page 3 of 3

INVENTOR(S) : Clarke et al

It is certified that error appears in the above-identified patent and that said Letters Patent is hereby corrected as shown below:

In the Claims

In claim 1, line 20, please rewrite "Tro" as --Trp--. At claim 2, line 3, please rewrite "Nicotanana" as --Nicotiana--. At claim 5, line 6, please rewrite "selfincompatible" as --self-incompatible--. Col.18,claim 5 line 14, please insert "Glp" to read --Gln --. At claim 5, line 16, please insert "Glp" to read --Gln --. At claim 5, line 19, please rewrite "Tro" as --Trp--.

Signed and Sealed this

Twenty-second Day of June, 1993

Attest:

MICHAEL K. KIRK

Attesting Officer

Acting Commissioner of Patents and Trademarks